United States Patent [19]
Robinson et al.

[11] Patent Number: 5,733,325
[45] Date of Patent: Mar. 31, 1998

[54] NON-MIGRATING VASCULAR PROSTHESIS AND MINIMALLY INVASIVE PLACEMENT SYSTEM

[75] Inventors: Timothy Robinson, Sandown, N.H.; Michael Weiser, Groton; John Carey, Lowell, both of Mass.; Dennis Kujawski, Brookline, N.H.

[73] Assignee: C. R. Bard, Inc., Murray Hill, N.J.

[21] Appl. No.: 643,527

[22] Filed: May 6, 1996

Related U.S. Application Data

[63] Continuation of Ser. No. 147,498, Nov. 4, 1993.

[51] Int. Cl.⁶ .................................................. A61F 2/06
[52] U.S. Cl. .................................................. 623/1
[58] Field of Search .............................. 623/1, 11, 12; 606/191, 198

[56] References Cited

U.S. PATENT DOCUMENTS

| | | | |
|---|---|---|---|
| 4,655,771 | 4/1987 | Wallsten | 623/1 |
| 5,064,435 | 11/1991 | Porter | 623/12 |
| 5,104,404 | 4/1992 | Wolff | 623/1 |
| 5,282,824 | 2/1994 | Gianturco | 606/198 |
| 5,290,305 | 3/1994 | Inoue | 606/191 |
| 5,330,500 | 7/1994 | Song | 606/198 |
| 5,354,308 | 10/1994 | Simon et al. | 606/198 |

FOREIGN PATENT DOCUMENTS

| | | | |
|---|---|---|---|
| 649051 | 1/1992 | Australia | 623/1 |
| 0464755 | 1/1992 | European Pat. Off. . | |
| 0472731 | 3/1992 | European Pat. Off. . | |
| 480667 | 4/1992 | European Pat. Off. | 623/1 |
| 539237 | 4/1993 | European Pat. Off. | 623/1 |
| 556850 | 8/1993 | European Pat. Off. | 623/1 |
| 0579523 | 1/1994 | European Pat. Off. . | |
| 579523 | 1/1994 | European Pat. Off. | 623/1 |
| 2671280 | 7/1992 | France | 623/1 |
| 511880 | 8/1991 | Japan . | |
| 5212121 | 8/1993 | Japan . | |
| 1217402 | 3/1986 | U.S.S.R. | 623/1 |
| 1457921 | 2/1989 | U.S.S.R. | 623/1 |
| 9112047 | 8/1991 | WIPO | 623/1 |
| 94001056 | 1/1994 | WIPO | 623/12 |

OTHER PUBLICATIONS

Irie, et al., "Relocatable Gianturco Expandable Metallic Stents", *Radiology*, vol. 178, No. 2, pp. 575–578.

*Primary Examiner*—Michael J. Milano
*Attorney, Agent, or Firm*—Arthur Z. Bookstein

[57] ABSTRACT

A graft assembly for securely positioning a graft at a predetermined location across an abdominal aortic aneurysm. The assembly includes a resilient self-expanding anchor that is secured to the graft. The anchor is characterized as being at least as long as the graft, and further as being adapted to be removed or repositioned at any time prior to complete deployment in the patient.

10 Claims, 10 Drawing Sheets

NON-MIGRATING VASCULAR PROSTHESIS AND MINIMALLY INVASIVE PLACEMENT SYSTEM

This is a continuation of application Ser. No. 08/147,498, filed Nov. 4, 1993.

FIELD OF THE INVENTION

The invention relates to devices and techniques for placing and securing a vascular graft in a predetermined location in a patient's vascular system.

BACKGROUND OF THE INVENTION

It has been long accepted practice to treat a variety of vascular disorders in a surgical procedure that involves placement of a vascular graft in a patient's vascular system. The construction and characteristic of the graft typically will be adapted to optimize its use in the specific surgical environment and condition to be treated and, accordingly, a number of different types of grafts are available. Among the most common types of vascular grafts are those formed from a woven or knitted tubular fabric as well as non-fabric tubes such as expanded polytetrafluoroethylene. Such grafts typically are placed in a patient's vascular system in a highly invasive surgical procedure. In general, the complexity of the surgical procedure required to place the graft will depend on many factors, including the location and surgical accessibility of the portion of the patient's vasculature where the graft is to be placed.

Not all vascular conditions in which it would be desirable to place a graft can be so treated. Among the particularly troublesome medical conditions in which it is desirable to place a graft is that of an abdominal aortic aneurysm, in which a portion of the patient's aorta, the major artery carrying blood from the heart, has developed a weakened wall such that the weakened portion will tend to expand under the influence of the patient's blood pressure. An aortic aneurysm presents a life threatening risk that the aneurysm may burst causing massive internal bleeding. Treatment of the condition typically has involved deeply invasive abdominal surgery in which the patient's abdominal cavity is opened to reach and expose the aortic aneurysm. While maintaining the patient on an independent life support system, the region of the aneurysm is incised lengthwise to enable insertion of the graft into the aorta to span the weakened region and define a structurally tubular flow path between the remaining healthy portions of the aorta. The graft so positioned then is sutured in place. The graft thus serves as a reinforcing liner for the weakened portion of the aorta. Such surgical procedures have been characterized by a relatively high mortality and morbidity rate. Typically, patients suffering from the condition are elderly and are less able to survive the rigors of major abdominal surgery. Additionally, there is a substantial degree of risk when the abdominal cavity is opened because the confining pressure of other abdominal organs on the aorta is released. In some cases, the abdominal wall in the region of the aneurysm is so weak that upon release of the confining pressure, the aneurysm bursts with resulting immediate massive hemorrhaging.

It would be desirable, therefore, to provide an apparatus, system and technique for placement of a graft, such as, but not limited to, placement in the abdominal aortic region, with a less invasive procedure that presents less risk to the patient. It is among the general objects of the invention to provide such a system.

BRIEF DESCRIPTION OF THE PRIOR ART

Mirich et al., in "Percutaneously Placed Endovascular Grafts for Aortic Aneurysms: Feasibility Study", *Radiology* (March 1989), describes the use of nylon covered, self expanding metallic stents to repair abdominal aortic aneurysms that were artificially produced in dogs. Mirich et al. describes a graft framework constructed from three self expanding metallic zigzag stents connected in tandem. The two lower stents are covered with nylon. The graft is anchored in position by barbs attached to both ends of the graft. Delivery of the framework is achieved by compressing the nylon covered graft and advancing it through a catheter with a blunt tipped introducer wire. When the nylon covered portion of the graft bridges the aneurysm, the introducer wire is held in place and the catheter slowly withdrawn. This releases the graft assembly and allows the stents to expand until they press against the vessel walls.

In a similar procedure, Lawrence Jr. et al., in "Percutaneous Endovascular Graft: Experimental Evaluation", *Radiology* (May 1987), discloses the use of an expanding stent of the type disclosed in U.S. Pat. No. 4,580,568 (Gianturco) to anchor and support a Dacron graft. The Gianturco stent comprises a wire formed into a closed zigzag configuration by creating an endless series of straight sections joined by bends. The stent is resiliently collapsible into a smaller generally tubular, low profile shape. In its compressed, low profile shape, the straight sections are arranged side-by-side, in close proximity, to facilitate insertion. The stent is resiliently expandable such that the straight sections press against the wall of the artery to maintain it open when the stent is permitted to resiliently expand.

The procedure disclosed by Lawrence Jr. et al. includes the use of a plurality of Gianturco stents in tandem. Dacron tubing is wrapped around the outside of the middle group of the stents, internalizing the stents within the graft. As a result, the lead and trail stents act as securing means, while the internal stents served to open the tubular graft when the device is released from the catheter. As with the procedure disclosed by Mirich et al., a catheter is used to deliver the graft framework to the treatment site.

The use of expanding stents is discussed further by Dobben et al. in "Prosthetic Urethra Dilatation with the Gianturco Self-expanding Metallic Stent: A Feasibility Study in Cadaver Specimens and Dogs", AJR 156:757–761 (April 1991). Dobben et al. describes the use of stainless steel stents bent into a zigzag pattern and then formed into a cylinder. Stents having flared ends as well as stents that are not flared are discussed. The stents are said to have been delivered to a predetermined location by using a coaxial Teflon introducer system. The flared stents were said to have been flared outwardly at both ends, and, when fully expanded, had a smaller diameter in the center than at the ends.

SUMMARY OF THE INVENTION

The present invention relates to a device, system and technique for the minimally invasive, percutaneous placement of a vascular graft, such as in the repair of an abdominal aortic aneurysm. The device comprises an implant which includes a tubular synthetic graft having proximal and distal ends and a resilient, self-expandng anchor of a length at least as long as that of the graft. In one embodiment, the anchor is formed from a single, continuous wire bent in a zigzag configuration to define a series of elongate wire segments connected by bends. The anchor defines a three-dimensional generally tubular structure having proximal and distal ends. The anchor is compressible to a low profile (small diameter) and can expand resiliently to an enlarged diameter. In a second embodiment, the anchor is formed of a pair of expandable segments, each formed of a single, continuous wire bent in a zigzag configuration. In the second embodiment, the two expandable segments are joined by at least two, substantially straight struts. In each case, the use of a single anchor having a length sufficient to span the length of the graft allows the physician to reposition or remove the graft if, during the graft implantation, it is determined that the graft is not positioned in the desired location or position.

In one aspect of the invention, the ends of the anchor may extend beyond the ends of the graft, and the exposed ends of the anchor may be curved outwardly. The curved ends of the anchor thus are adapted to bear against the wall of the blood vessel at a plurality of points (in the region of the bends) rather than along the full length of the anchor. By so concentrating the points of contact of the anchor with the blood vessel, a more secure attachment of the anchor to the vessel wall is achieved, thereby reducing the risk of the device migrating downstream in the blood vessel.

In another aspect of the invention, the anchor is intended to maintain close contact with the graft along its entire mutual length. By minimizing the extent to which portions of the anchor protrude radially inwardly into the graft, the cross-sectional area of the lumen through the graft is not compromised. This is desirable, for example, should it be necessary to subsequently treat the patient with a catheter that must be passed through the graft. The absence of radially inwardly protruding anchor portions reduces the risk that the subsequently introduced catheter or other vascularly insertable member might become caught on the anchor.

In still another aspect of the invention, the graft may surround the anchor or the anchor may surround the graft. Additionally, embodiments in which some longitudinal elements of the anchor are contained within the graft and other longitudinal elements are positioned on the outside of the graft are contemplated as well.

Although the anchor may be attached to the graft by sutures, in a further aspect of the invention, it is preferred to capture a marginal end portion of the graft within a pair of wires that define a portion of the anchor. The wire portions may be joined in a manner that captures a marginal end portion of the graft without the use of bulky sutures.

Attachment of the anchor to the vessel wall may further be enhanced by one or more radially outwardly protruding hooks attached to the anchor. The hooks engage the vessel wall under the influence of the resilient anchor and enhance the anchor's resistance to migration once the graft is properly positioned. The hooks preferably are formed on the end of short segments of wire that are welded to the anchor to locate the hooks at regions adjacent to the distal bends. The hooks extend a short distance beyond the bends and become engaged in the blood vessel wall once the anchor is expanded.

The graft assembly can be delivered percutaneously with a catheter-like delivery device that includes an outer sheath and an inner positioning member that extends through the outer sheath. The graft assembly is compacted to its low profile configuration and is loaded within the distal end of the sheath. The delivery device then is advanced into the patient's vascular system in an over-the-wire technique. The positioning member has a hollow lumen adapted to receive the guidewire. When the delivery system and graft assembly have been advanced to the intended site of deployment, the positioning member is held stationary while the sheath is withdrawn. As the sheath withdraws, the anchor and graft are progressively exposed so that the anchor can expand and resiliently engage the wall of the blood vessel.

It is among the general objects of the invention to provide a percutaneously deliverable vascular prosthesis that can be repositioned or removed prior to completion of an implantation procedure.

It is another object of the invention to provide an improved percutaneously deliverable vascular prosthesis that avoids post implantation migration.

Another object of the invention is to provide an improved system and technique for more securely anchoring and positioning the vascular graft within a blood vessel.

A further object of the invention is to provide an improved technique for treating a vascular aneurysm.

Another object of the invention is to provide a percutaneously placeable graft assembly that includes a graft and a resiliently expandable anchor attached to the graft in which the anchor is configured to concentrate the expansion force developed by the anchor at a plurality of discrete locations.

BRIEF DESCRIPTION OF THE DRAWINGS

The foregoing and other objects and advantages of the invention will be appreciated more fully from the following further description thereof, with reference to the accompanying drawings wherein.

DETAILED DESCRIPTION OF THE INVENTION

Figure 1:
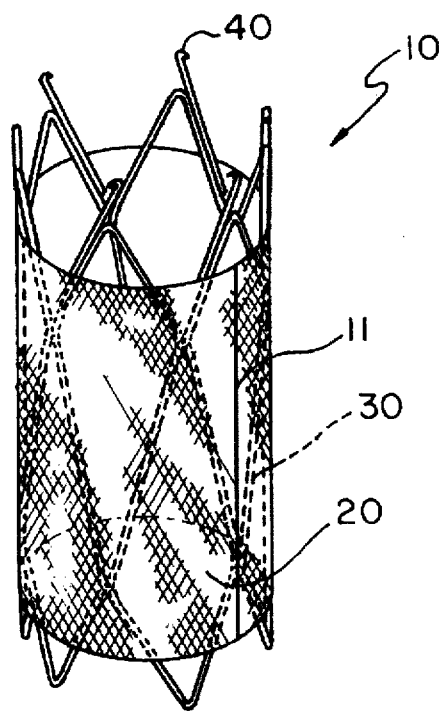
FIG. 1 is a side elevation of one embodiment of the implant assembly.

FIG. 1 illustrates one embodiment of an implant assembly, indicated generally at 10, adapted for use in the present invention. The assembly 10 includes a synthetic vascular graft 20 and an anchor 30 which are intended to be placed within a patient's blood vessel, the invention being described, for example, in connection with the treatment of an abdominal aneurysm. The graft 20 is tubular and may be formed from materials and in any of a variety of constructions known in the art. For example, the graft may be formed from expanded polytetrafluoroethylene with a porosity and internodal distance similar to grafts presently commercially available. Alternately, the graft may be formed from a fabric material, either woven or knitted, or in other configurations known in the art. Preferably, the graft has a porosity that will exhibit the desired properties of promoting tissue ingrowth while precluding undesired blood leakage. The graft can be provided with one or more radiopaque stripes 11 to facilitate fluoroscopic or X-ray observation of the graft. The stripes may be formed in the graft by any conventional means as will be appreciated by those skilled in the art. The implant assembly 10 also includes an anchor 30 that is secured to the graft and serves to retain the graft in position in the blood vessel. The anchor may be positioned either on the interior or the exterior of the graft.

Figure 2:
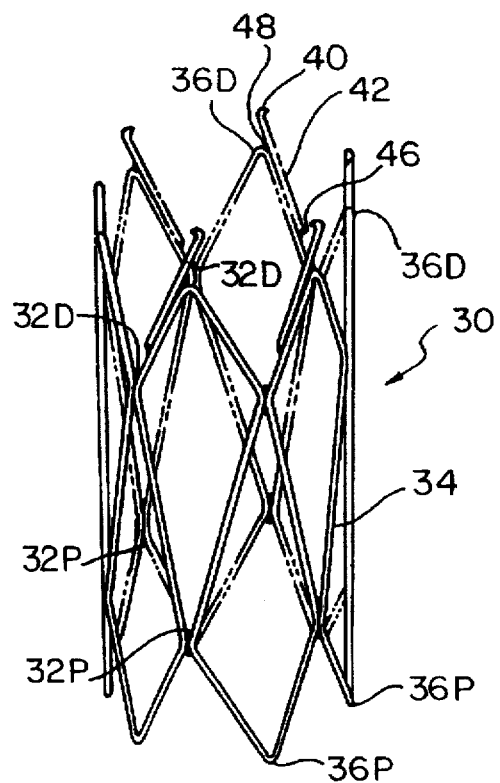
FIG. 2 is a side elevation of an anchor for use with the implant of FIG. 1.

FIG. 2 shows, somewhat diagrammatically, a first embodiment of the anchor 30. For clarity, a portion of the anchor has been drawn in phantom. The anchor 30 can be made from a single continuous length of metal wire. The wire preferably may be an alloy of nickel (35%), cobalt (35%), chromium (20%), and molybdenum (10%). Such wire is commonly available from a number of suppliers under the designation MP35N. The alloy has high corrosion resistance, is non-magnetic and has a strength comparable to stainless steel. The wire is formed to define a series of wire segments 34 and alternating proximal and distal bends 36P, 36D. The segments 34 and bends 36P, 36D are arranged in a zigzag pattern. The wire segments 34 preferably have the same length. In making the anchor a wire, so bent, is attached, as by welding, at its ends to form a three-dimensional, generally tubular structure. In addition, each of the wire segments 34 is connected to the two segments adjacent to either side of it by welds 32P and 32D. Thus, between each of the proximal and distal bends, 36P, 36D is a pair of welds 32P, 32D that join the segment 34 connecting the proximal and distal bends to the segments positioned adjacent to it on either side.

The resulting anchor is resilient and can be compressed to a low profile, small diameter configuration suited for percutaneous delivery into the patient's vascular system. In addition, the provision of the welds to join adjacent wire segments provides the anchor with varying degrees of radial force along its axial length. It is desired that the radial forces be greatest at the axial ends of the implant, with the middle section exhibiting a weaker axial force. That effect can be achieved by joining each segment to its adjacent segments in the manner described. Furthermore, as detailed below, grafts having a single anchor extending along their entire length are adapted for removal during the implantation process if so desired.

In accordance with the invention, if the anchor is of a length such that one or both ends extend beyond the graft, either one or both of the portions of the anchor segments 34 which extend beyond the graft can be curved so as to provide enhanced anchoring capabilities. In that case, the bends 36P and/or 36D provide point-to-point contact with the blood vessel wall, thereby enhancing the anchoring by providing localized areas of high contact force.

The security of the engagement between the anchor 30 and the aorta wall may be further enhanced by hooks suggested diagrammatically at 40, which are secured to the anchor 30. The hooks 40, as suggested in FIG. 2, are formed on the distal ends of hook wire segments 42. The hook wire segments 42 preferably are formed from the same material as the main wire of the anchor 30. They are secured along the anchor segments 34, such that the hooks 40 are disposed beyond the distal bends 36D. The segments 42 are welded to the anchor segment 34 at first (proximal) and second (distal) junctions 46, 48. The hooks 40 preferably are sharp and aid in attaching the anchor 30 to the aorta wall to prevent migration after the device is implanted. It should be understood that although FIG. 1 illustrates a hook associated with each of the anchor segments 34, it may not be necessary to include a hook for each anchor segment. The curved configuration of the anchor segments serves several purposes. It results in a decrease in the surface area along which the anchor 30 engages the vessel wall. That, in turn, concentrates the resilient expansion force of the anchor at the point-like regions of contact of the bends 36P, 36D and hooks 40 so that they will tend to more firmly dig into and bear against the vessel wall. The anchor segment 34 may be curved to include an arc of between about 5° to about 30°.

Figure 3:
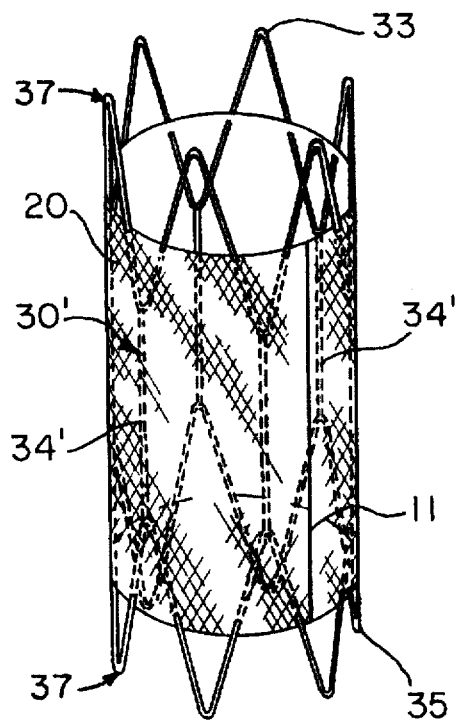
FIG. 3 is a side elevation of a second embodiment of the implant assembly.
Figure 4:
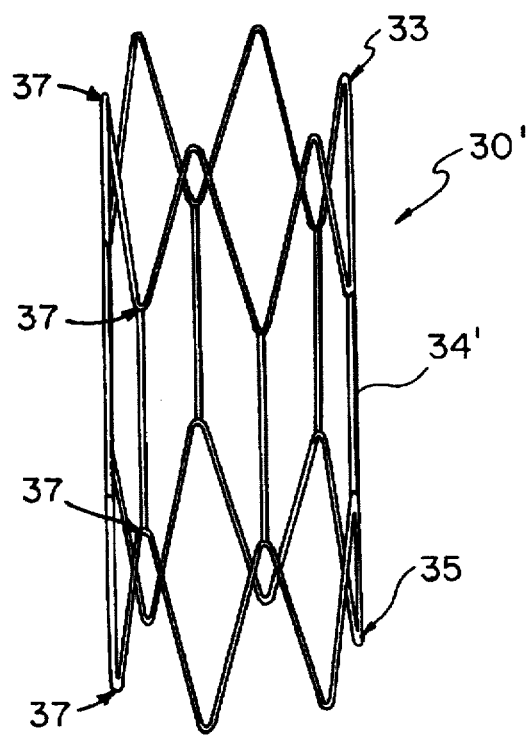
FIG. 4 is a side elevation of an anchor assembly for use with the implant of FIG. 3.

A second embodiment of the graft assembly is shown in FIGS. 3 and 4. In that embodiment, the graft 20 is of the same construction as described above. The anchor 30', however, is formed of a pair of expandable segments 33, 35 each joined by at least two longitudinal struts 34'. Each of the expandable segments 33, 35 is formed of a single continuous segment of wire having a series of zigzag bends 37. The struts 34' extend between the expandable segments 33, 35, being welded between the proximal end of one segment 33 and the distal end of the other segment 35. The anchor 30' may be positioned on either the inside or the outside of the graft 20. Additionally, in one embodiment, the anchor may be mounted such that some struts are positioned on the inside of the graft while other struts are positioned on the outside of the graft.

As with the previously described embodiment, the anchor 30' may be of a length such that one or both ends extend beyond the graft. Additionally, one or both of the segments, if extending beyond the graft, may be curved to assist in maintaining the graft in position in a blood vessel. Also, hooks extending from the anchor may be used to further aid in maintaining the position of the implant. Finally, as in the earlier embodiment, the use of an anchor extending along the entire length of the implant allows the implant to be removed during the implantation procedure if desired.

Figure 5:
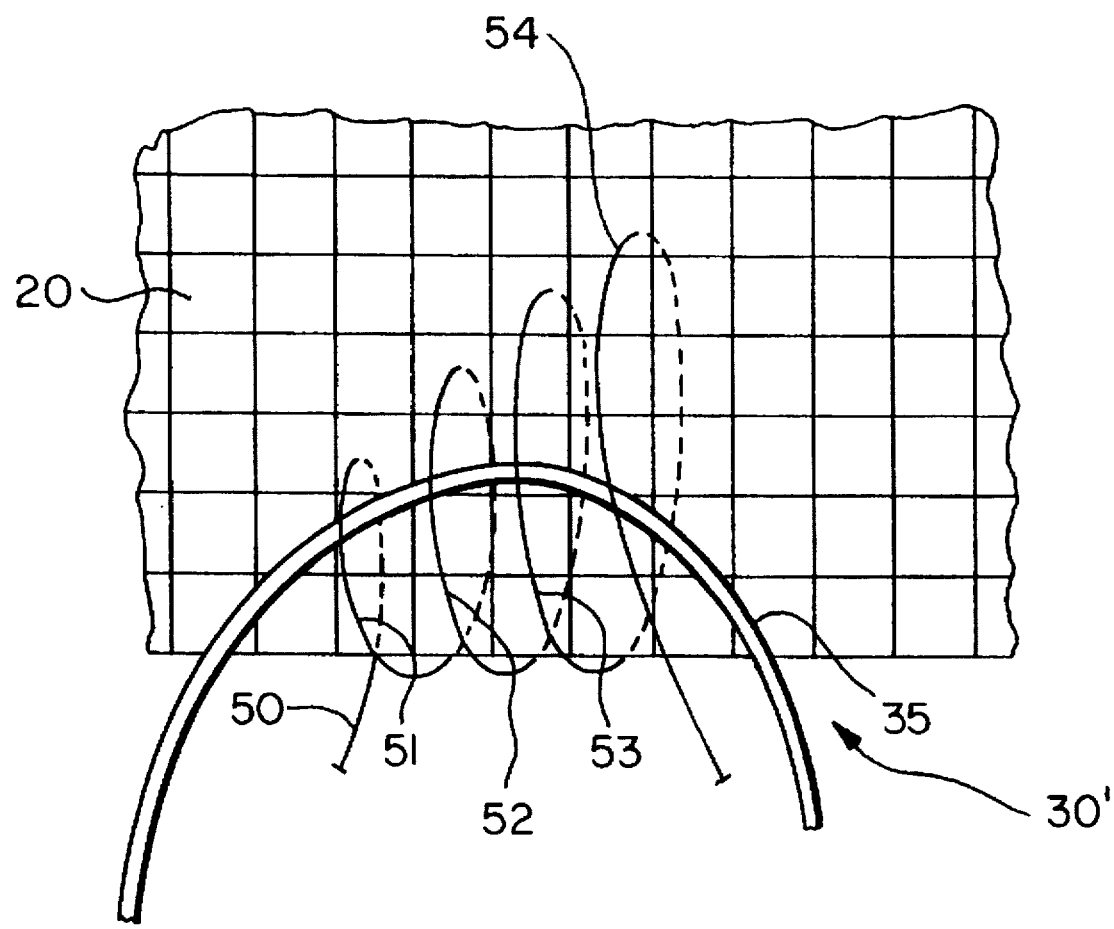
FIG. 5 is a diagrammatic illustration of the use of sutures to attach an anchor to a graft.

Either anchor 30, 30' may be secured to the graft 20 by sutures. In the case of the first embodiment anchor 30, the suture preferably secures the anchors at the welds 32D, 32P. In the case of the second embodiment anchor 30', the suture preferably secures the anchor at the proximal bends of the distal anchor segment 33 and at the distal ends of proximal anchor segment 35. As shown in FIG. 5, anchor 30' may be secured to the graft by suturing the bends of segment 35 of anchor 30' to the graft 20. The suture 50 is passed through the mesh of the graft 20 and around a portion of the anchor. Preferably, the suture 50 is passed about the securing section of the anchor four times, with each successive stitch 51, 52, 53, 54 being further removed from the bend.

Figure 6:
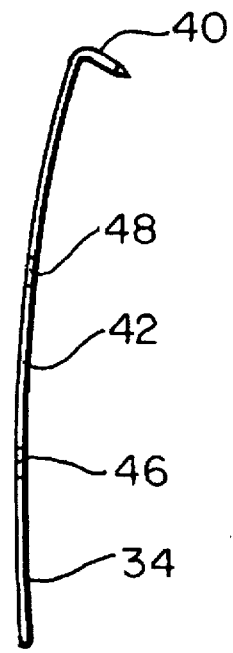
FIG. 6 is an illustration of an anchor segment and attached hook.
Figure 7:
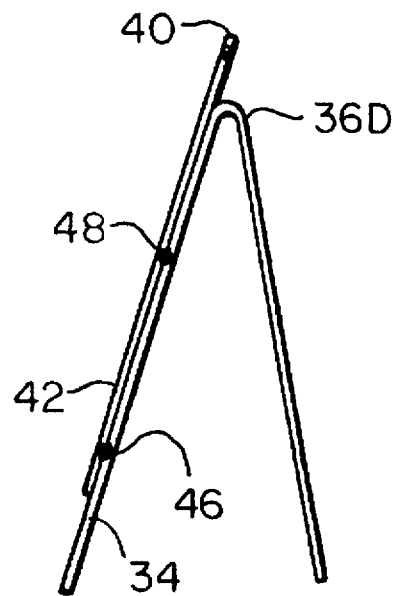
FIG. 7 is an illustration of a portion of the anchor as seen from the right of FIG. 6.

FIGS. 6 and 7 illustrate, in more representative detail the configuration of a segment 34 of an anchor in accordance with the invention. The segment 34 of FIG. 6 is curved in the manner described above, however such curvature is optional. In the curved configuration, the wire segments 42 that support the hooks 40 extend more fully toward the proximal bend 36P than in the configurations illustrated in FIGS. 2 and 4, respectively.

By way of dimensional example, in an anchor adapted for use in an abdominal aortic aneurysm repair prosthesis as illustrated in FIGS. 1 and 2, the hook wire segment 42 on which the hook 40 is formed may be of the order of ⅞ of an inch long with the hook 40 being disposed approximately ⅛ of an inch above the distal bend 34D associated with that hook. The wire from which the anchor and the hook segment are made may be of the order of 0.014 inches diameter. The proximal and distal resistance welds by which the hook segment is secured to the anchor segment may be disposed, respectively, about ⅔ of an inch and about ¼ of an inch from the distal bend 36D. FIG. 6 illustrates a representative degree of optional curvature for the wire segment and an associated hook segment. By way of example, the degree of curvature may be of the order of 3 inches in radius. The relaxed expanded diameter of the anchor 30 may be between about 10 mm to 40 mm, depending on the blood vessel into which it is to be placed.

Figure 8:
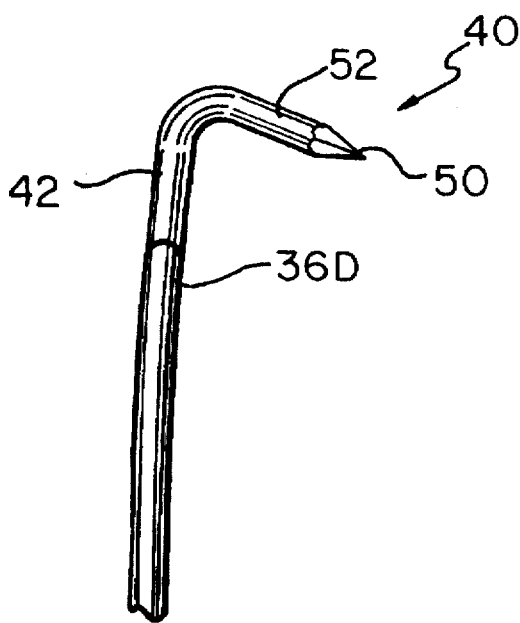
FIG. 8 is an enlarged illustration of the hook arrangement in FIG. 6.
Figure 9:
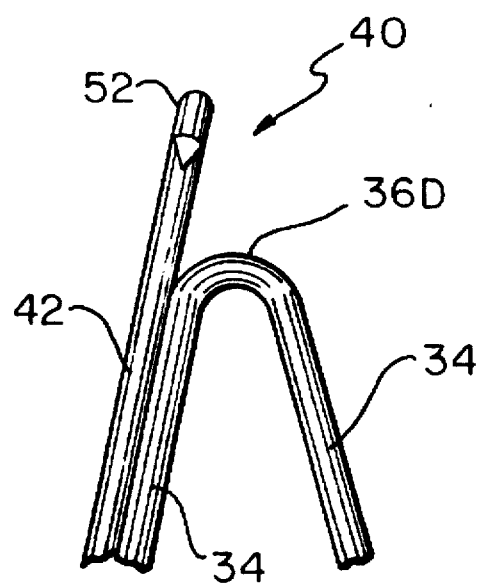
FIG. 9 is an enlarged illustration of the hook arrangement in FIG. 7.

FIGS. 8 and 9 illustrate in enlarged detail the configuration of a typical hook 40 and its associated bend. Again, for purposes of illustration the anchor 30 of FIGS. 1 and 2 has been shown. The hook is provided with a sharpened tip 50 formed at the end of a generally radially outwardly protruding portion 52. The protruding portion which may be of the order of 0.050 inches long and may be formed by bending the hook wire 42 from which the hook is formed about a pin of the order of 0.050 inches in diameter. The bends 36P, 36D may be formed by bending the wire about a pin of the order of 0.100 inches in diameter.

Figure 10:
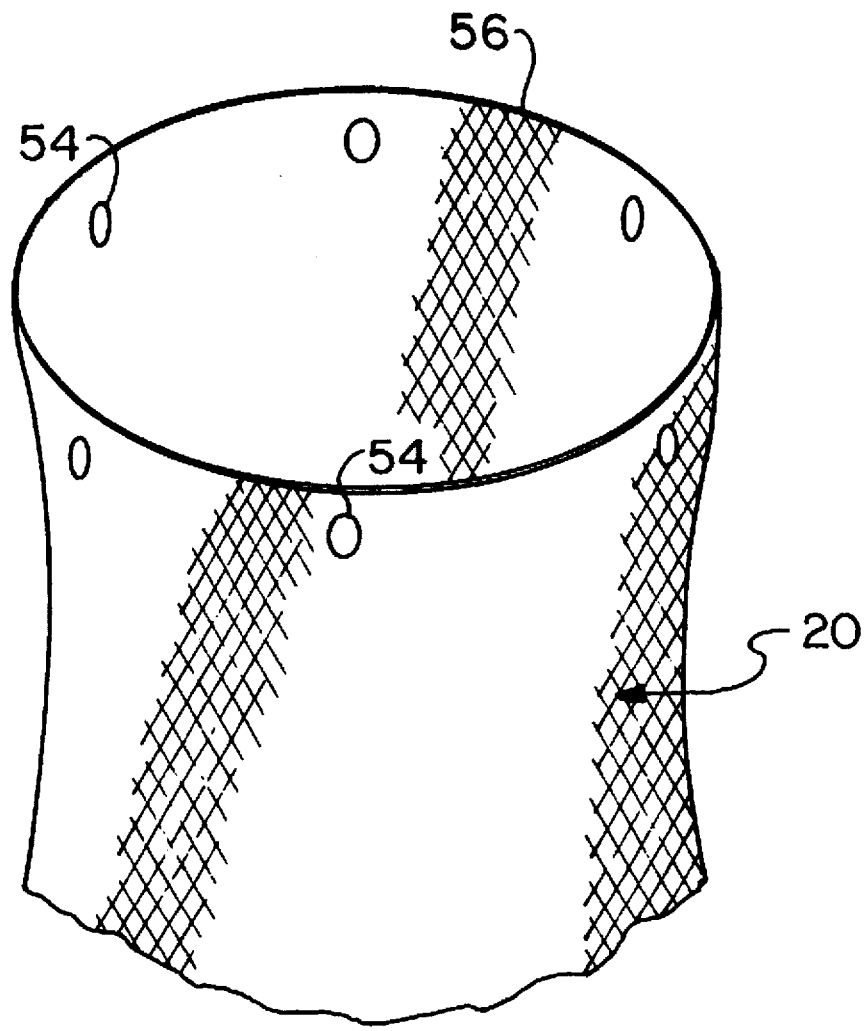
FIG. 10 is an illustration of the distal end of a graft having holes adapted to receive and be attached to an anchor.
Figure 12:
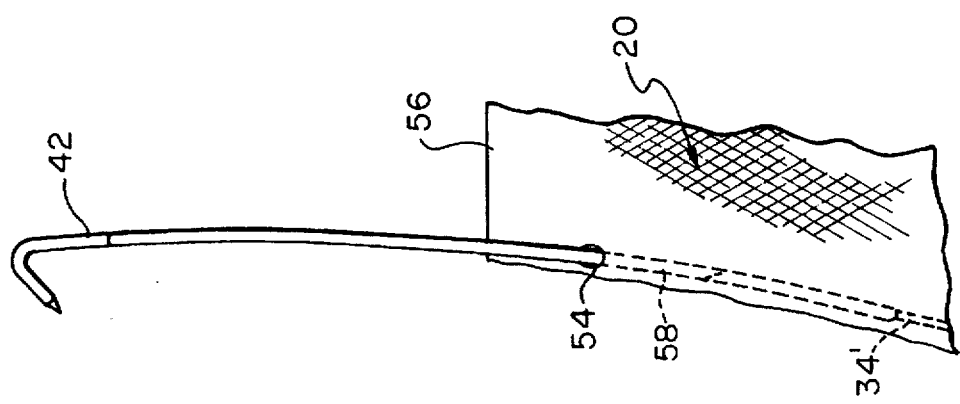
FIGS. 11 and 12 are illustrations of the manner in which an anchor may be attached to the graft as shown in FIG. 10.
Figure 11:
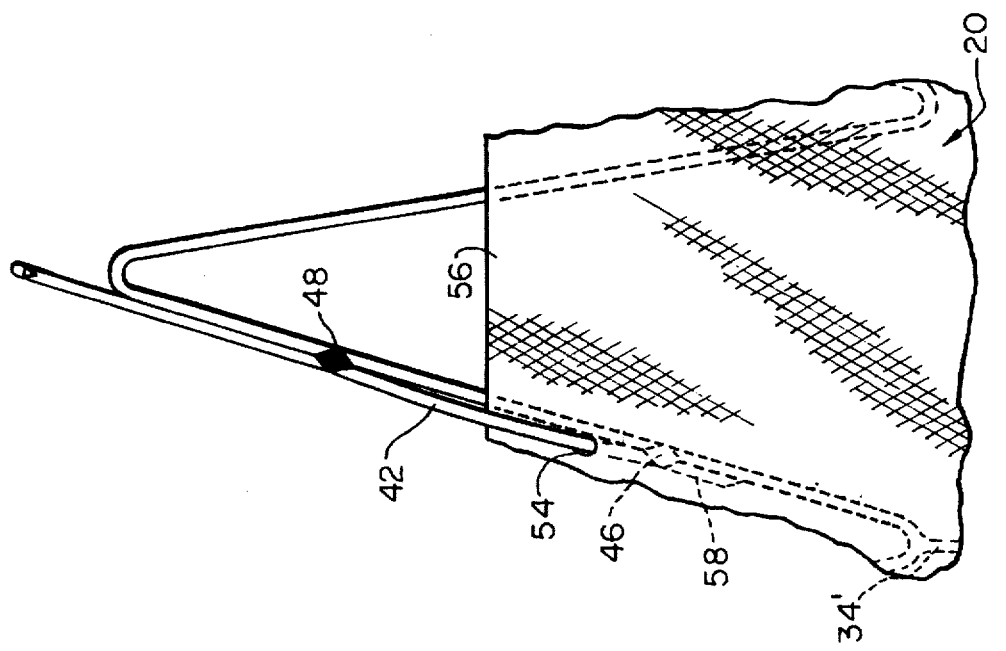
Figure 13:
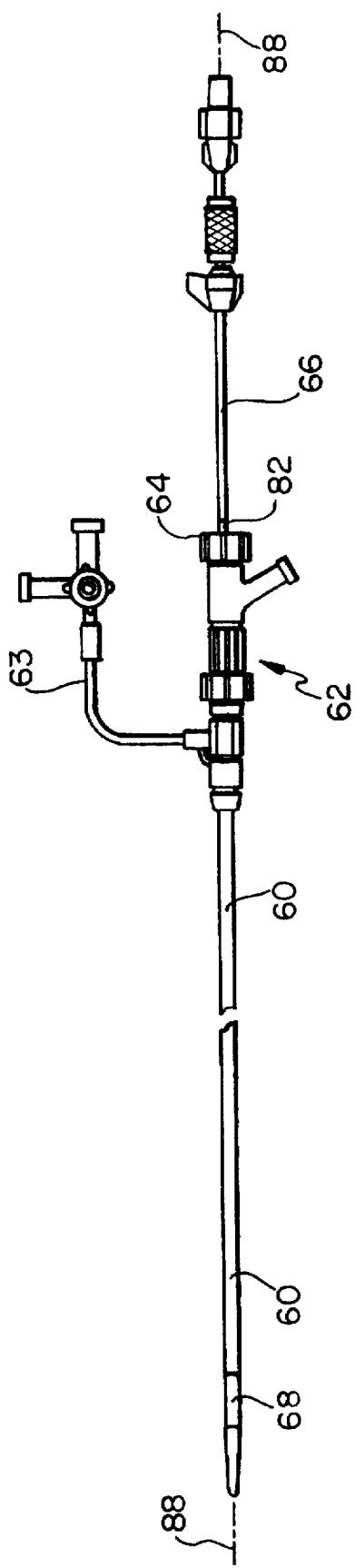
FIG. 13 is an illustration of the delivery device for the implant assembly.

FIGS. 10, 11 and 12 illustrate portions of an assembly incorporating the hook configuration of FIGS. 6–9 and an improved arrangement for attaching the graft 20 to the anchor 30' of FIG. 4. As shown in FIG. 10, the distal end of the graft 20 is formed to include a plurality of circumferentially spaced holes 54 disposed slightly proximally of the distal edge 56 of the graft. All edges of the graft including the distal edge 56 as well as the edges defined by the holes may be heat sealed or otherwise treated, if necessary, to prevent unraveling of the graft. By way of example, for an anchor 30' configured as described above (FIG. 4), the holes 54 may be of the order of 0.016 inches diameter and may be spaced approximately 2 mm from the distal edge 56 of the graft. FIGS. 11 and 12 illustrate the manner in which the anchor is joined to the graft. After the anchor 30' is formed as described above, the hook segment 42 is joined to the anchor, such as by resistance welding, but only at one of the junctures 46, 48, and preferably, at the proximal juncture 46. When the desired number of hook segments 42 have been attached to the anchor segment 33, the anchor is inserted into the the graft 20 and positioned to allow a portion of each hook segment 42 to extend out of the graft through the holes 54. The position of the anchor 30' is adjusted until the distal, unattached portion of each hook wire segment 42 overlies the outside of the distal margin of the graft while its proximal end 58 and proximal juncture 46 are positioned on the graft interior just proximally to the holes 54. With the graft and anchor so assembled, the distal juncture 48 can be made using a weld or the like. Thus, the marginal portion of the graft is captured between the generally parallel anchor segments 34 and associated hook segments 42 between the proximal and distal junctures 46, 48. This arrangement is preferred to a sutured connection between the anchor and graft in that it cannot become unraveled and, additionally, is less bulky than the sutured connection.

In the preferred embodiment of the invention, the implant is selected so that when fully expanded, it will match or be slightly larger in diameter than the vessel to which it is to be implanted. It is intended that when the implant is deployed and expanded, the ends of the graft will lie as close to the surface of the lumen of the blood vessel as possible in order to enhance tissue ingrowth into the graft wall and provide a smooth transition in the surface that defines the flow area from the healthy portion of the blood vessel into the graft. To that end, the anchor should be selected with respect to the graft so that the relaxed, freely expanded anchor will define a diameter greater than the fully expanded diameter of the graft. That assures that when the device is deployed, the anchor will open the end of the graft fully.

FIGS. 13–16 illustrate the catheter-like device by which the implant assembly may be percutaneously inserted and deployed within the patient's blood vessel. The delivery device includes an elongate flexible sheath 60 formed from a suitable polymeric material and having a fitting 62, including a Tuohy-Borst adapter 64 at its proximal end. The sheath 60 is adapted to receive a positioning tube 66 that has, at its distal tip, a flexible distally tapered dilator 68 and a stay 78 located proximally of the dilator tip. The proximal end 72 of the dilator tip is dimensioned to be received within the lumen at the distal end of the flexible sheath. The positioning tube 66 is longer than the sheath 60 so that when assembled, the proximal end of the tube 66 will protrude proximally of the Tuohy-Borst sheath adaptor The positioning tube 66 is adapted to receive a guidewire 88 to facilitate placement of the device. The device may also be provided with a side arm 63. The side arm provides a channel through which a fluid, such as a radiopaque dye, may be injected into the patient to aid in fluoroscopic vizualization during the implantation procedure.

Figure 14:
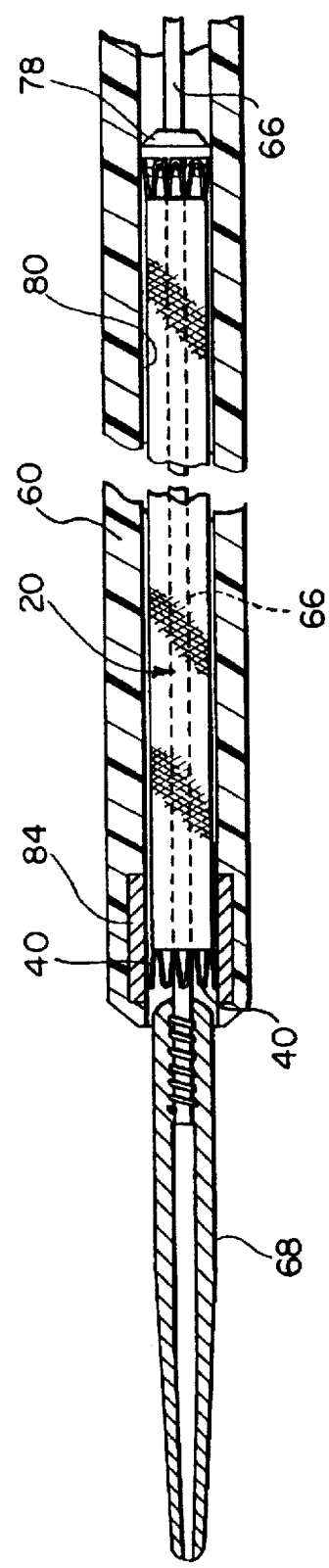
FIG. 14 is an enlarged sectional illustration of the distal region of the delivery device loaded with the implant assembly and in readiness for insertion into the patient.

When the delivery device and graft assembly are arranged in readiness for insertion into the patient, the graft assembly will be contained within the distal end of the sheath 60 and about a portion of the positioning tube as illustrated in enlarged detail in FIG. 14. As suggested diagrammatically in FIG. 15, the graft assembly is loaded into the delivery device using a funnel-like loader 70 having an enlarged distal inlet end 72 and a narrowed proximal outlet end 74.

Figure 15:
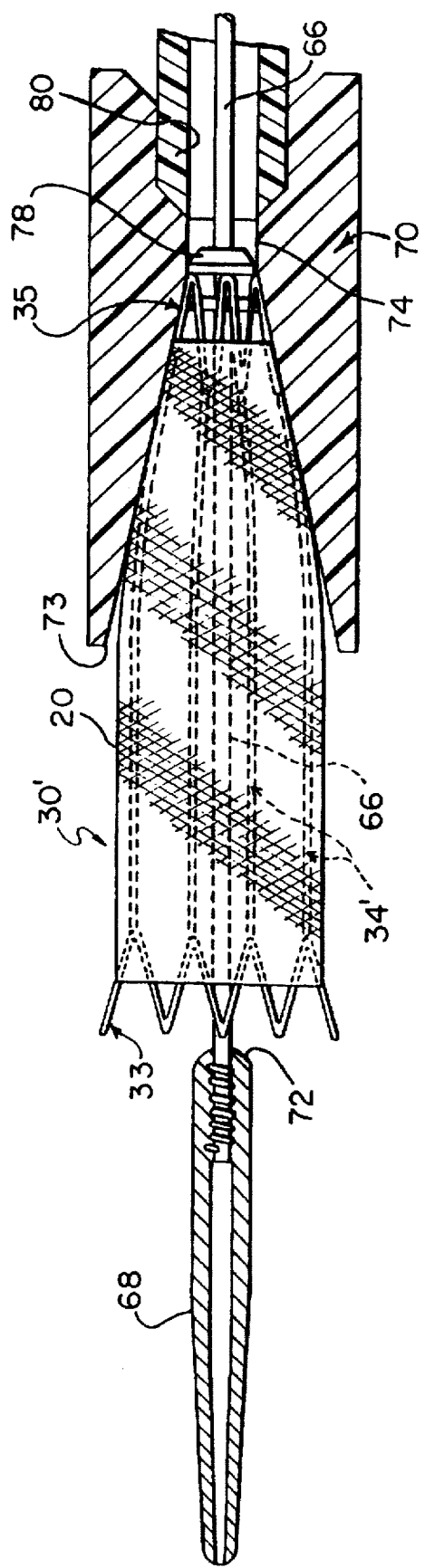
FIG. 15 is a diagrammatic illustration of the manner in which the graft assembly may be loaded into the distal end of the delivery device.

FIG. 15, which is diagrammatic and not to scale, illustrates the configuration of the delivery device when loading the graft assembly. The positioning tube 66 is extended through the sheath with its distal end extending beyond the distal tip of the sheath so that a stay 78 is spaced a short distance from the distal end of the sheath 60. The funnel 70 is disposed about the positioning tube 66 with the proximal end of the funnel being in communication with the distal outlet end of the sheath. The graft assembly is placed over the distal end of the positioning tube 66 in a position such that the proximal bends of anchor segment 35 are disposed against the stay 78. The graft assembly then is pushed into the funnel to compress the proximal end of the anchor, and move the anchor, stay, and positioning tube into the lumen 80 at the distal end of the sheath. As the positioning tube and graft assembly are pushed through the funnel 70, the graft is progressively constricted to a low profile about the positioning tube. Consequently, as the graft assembly constricts about the positioning tube 66 both are advanced into the distal end of the sheath, with the anchor compressed to a low profile with its proximal bends bearing against the distal face of the stay 78.

Figure 16B:
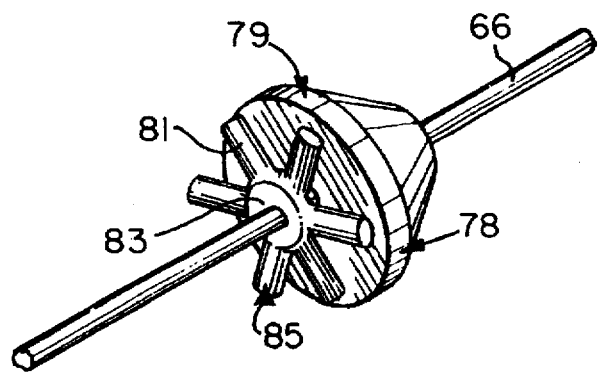
FIGS. 16a–16c are diagrammatic illustrations of a section of the delivery device which engages the proximal end of the implant.
Figure 16A:
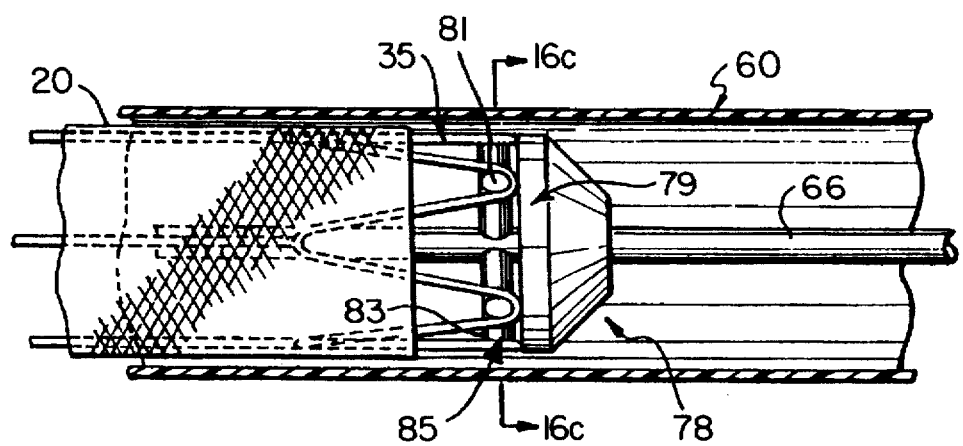
Figure 16C:
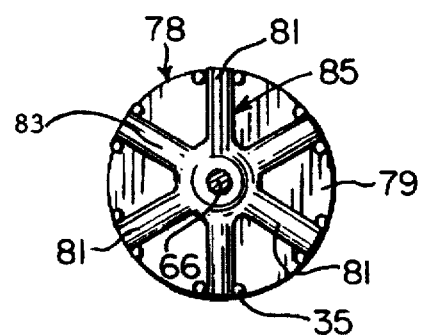

As shown in FIGS. 16a–16c, the stay 78 which is used to maintain the position of the implant 10 as the sheath 60 is withdrawn operates in conjunction with an implant retention device 85. The retention device 85 takes the form of a plurality of radially extending spokes 81 attached to a central hub 83. The retention device 85 may be mounted on the positioning tube 66 a short distance distally to the stay 78, or it may be formed as an integral part of the stay. As can be seen most clearly in FIG. 16a, in extending radially, the spokes 81 of the retention device 85 engage the proximal-most ends of the anchor 30, 30' when the proximal portion of the anchor is compressed within the sheath 60. The engagement is achieved by a distal portion of each spoke which becomes seated in the space on the interior of the bends at the proximal end of the anchor. The result is that the anchor, (and thus, the entire implant), is prevented from moving distally relative to the stay. In so doing, if removal or repositioning of the implant is desired, the sheath 60 may be advanced distally to recapture the implant assembly. Since the proximal-most bends of the implant assembly are retained by the radial spokes 81, the implant is prevented from moving in the distal direction as the sheath is advanced.

Once the implant has been positioned in its final location, the sheath is fully withdrawn, thereby allowing the proximal-most section of the anchor to expand outwardly into contact with the blood vessel wall. Upon expansion, the proximal portion of the anchor is released from the retention assembly 85, as the anchor expands radially beyond the ends of the spokes. In so doing, the implant assembly is released from the delivery device and deployed within the blood vessel.

The tube 66 preferably is provided with a marker 82 (FIG. 13) near its proximal end, the marker being located so that when it is exposed proximally of the fitting 62, the graft assembly will have been withdrawn fully into the distal end of the sheath and the proximal end of the dilator tip also is drawn slightly into the distal tip of the sheath, as shown in FIG. 14. The distal tip of the sheath preferably is provided with an inner lining segment 84 formed from a relatively hard material. The lining segment is dimensioned and located to be aligned with the hooks on the distal end of the distal anchor and serves to prevent the hooks 40 from digging into the softer material from which the sheath is formed. Additionally, the distal liner preferably is formed from a material sufficiently dense to be observed under fluoroscopy. When the device is thus loaded, it is in readiness for insertion into the patient and deployment of the graft assembly.

The device can be inserted percutaneously into the patient's vasculature with the aid of a guidewire. The guidewire 88 may be preliminarily loaded into the lumen of the positioning tube before the delivery device is inserted into the patient or, alternately, the guidewire may be placed separately in a preliminary procedure into the patient's blood vessel. In either case, the delivery device is advanced into the patient's blood vessel, for example, as through the femoral artery when placing a graft assembly to treat an abdominal aneurysm. The guidewire may be advanced independently toward and through the region to be treated. The delivery assembly then may be advanced over the guidewire until the graft assembly is in its intended position. In the case of an abdominal aortic aneurysm, the device would be located so that the distal anchor is located distally of the region of the aneurysm such that the graft, when deployed, can pass through the aneurysm thereby lining the artery. With the delivery device so placed, the position of the positioning tube is maintained while the sheath is withdrawn in a proximal direction. The stationary stay maintains engagement with the proximal end of the anchor in the manner described above, thereby preventing proximal movement of the graft assembly while the sheath is withdrawn. As the sheath is progressively withdrawn and the anchor emerges from the distal end of the sheath, the anchor expands into engagement with the inner luminal surface of the blood vessel while simultaneously expanding the distal end of the graft.

The implants are characterized in their ability to be removed or repositioned from the patient prior to completion of the deployment process. In particular, as long as a portion of the implant is maintained within the sheath, the deployment process can be reversed to recapture the implant within the sheath and reposition or remove it. As discussed above, progressive withdrawal of the sheath exposes progressive lengths of the implant which expand into contact with the blood vessel walls. During this procedure, fluoroscopic visualization methods can be used to determine if the implant is being positioned as desired.

If the positioning is as desired, the sheath is withdrawn along the entire length of the implant, thereby releasing the implant and allowing it to expand into contact with the blood vessel along the entire length of the implant. However, if it is determined prior to complete withdrawal of the sheath (and concurrent release of the implant) that the implant is not positioned exactly as desired, the sheath can be advanced distally to recapture the implant. Since, in each embodiment, the implant includes a single anchor assembly along the entire length of the graft, compression of the proximal end of the graft, such as by advancing the sheath, allows the compression force to be communicated distally. As a result, the sheath may be advanced over the entire implant assembly, progressively collapsing and recapturing the implant.

In contrast, implants having a distal anchor and, optionally, a separate proximal anchor, cannot be recaptured following release of the distal anchor from a sheath since there is no mechanism for holding and recompressing (i.e., recapturing) that anchor. Furthermore, even if one were to use fluoroscopic visualization methods to determine the positioning of the implant prior to complete release of the distal anchor, it is unlikely that satisfactory results could be achieved since an insufficient amount of the implant would be exposed to determine its ultimate location and position.

Figure 17A:
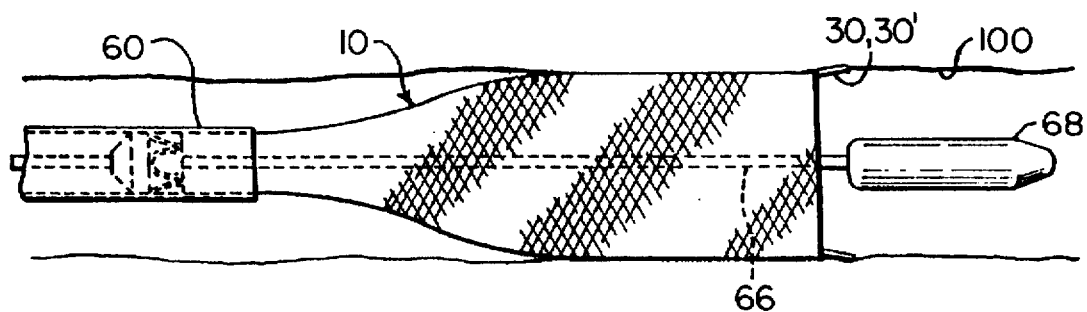
FIGS. 17a–17c are diagrammatic illustrations of the process by which an implant may be recaptured during an implantation procedure.
Figure 17B:
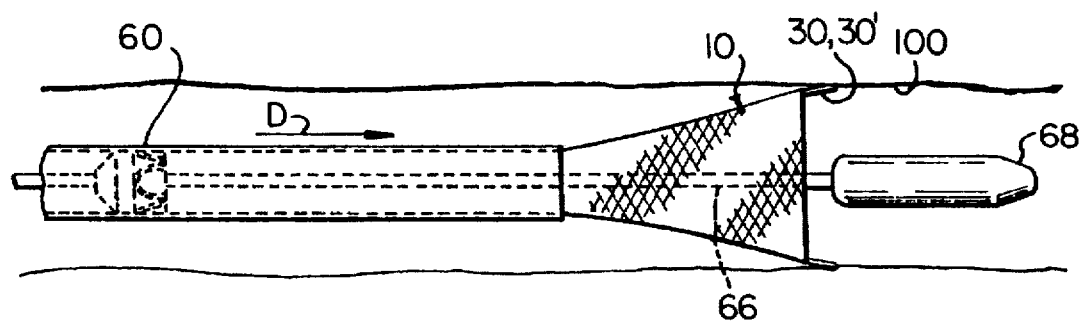
Figure 17C:
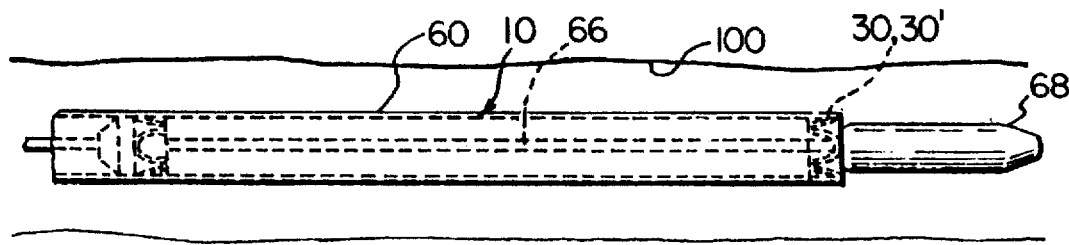

FIGS. 17a–17c depict the implant removal process described above. In FIG. 17a, an implant 10 having either an anchor 30 of the embodiment shown in FIG. 2 or anchor 30' of the embodiment shown in FIG. 4 is partially released from the delivery sheath 60. The distal end of the implant has deployed and seated against the wall of the blood vessel 100. If at this point it is determined, such as by fluoroscopic vizualization, that repositioning or removal of the implant is required, the sheath can be advanced distally to progressively recapture the implant. As shown in FIG. 17b, the sheath 60 has been advanced in the distal direction D causing compression and recapture of a portion of the implant 10. The compression forces on the proximal end of the implant are transferred to its distal end, causing the distal end to begin contracting as well. In FIG. 17c, the sheath has been advanced over the entire length of the implant. In so doing, the implant has been removed from contact with the vessel wall and can be removed from the patient or positioned at a different location.

It should also be appreciated that the scope of the invention is not confined to the specific embodiments illustrated and described herein. Rather, it is the intention of the applicant that the scope of the invention be determined by the appended claims and their equivalents.

We claim:

1. A removable repair assembly for placement in a blood vessel which comprises:

an elongate tubular graft having an interior surface, an exterior surface, a proximal end, a distal end, and an axial length; and an anchor assembly having a proximal end, a distal end and an axial length greater than the axial length of the graft;

the anchor assembly having, at each end, an anchor that is radially resiliently expandable from a radially contracted to a radially expanded configuration, the proximal and distal anchors being connected to each other by at least two longitudinal struts, each of the struts extending between the proximal and distal anchors;

the struts being connected to the proximal and distal anchors to cause a radial contraction force applied at one of the anchors to be transmitted to the other of the anchors, the struts serving to maintain the lengthwise positions of the proximal and distal anchors, the struts being arranged in the repair assembly such that they do not develop any radially outward expansion force independently of their connection to the proximal and distal anchors;

the end of at least one of the anchors protruding beyond its associated end of the graft and defining a connector for direct, rigid connection to a delivery device.

2. A repair assembly as in claim 1 wherein the anchor assembly is secured to the interior surface of the graft.

3. A repair assembly as in claim 1 wherein the anchor assembly is secured to the exterior surface of the graft.

4. A repair assembly as in claim 1 wherein the resilient expansion force is developed solely within and by the resilience of the proximal and distal anchors.

5. A repair assembly as in claim 1 wherein at least one of the self-expanding segments comprises a single continuous segment of wire having a series of bends.

6. A repair assembly as defined in claim 1 wherein the protruding end of the anchor defines at least one bight directly connectible to a delivery device.

7. A repair assembly as defined in claim 6 wherein said at least one anchor is formed from a zigzag wire including longitudinal segments connected by bends at adjacent ends of adjacent longitudinal segments, the protruding portions of the longitudinal segments and their associated bends defining said bights.

8. A repair assembly as defined in claim 4 and a delivery device in combination therewith, the combination further comprising:

a tubular sheath receptive to the repair assembly for maintaining the repair assembly in a radially compressed configuration, the sheath being open at its distal end with the repair assembly contained within the sheath;

a retainer movable axially relative to the sheath, the retainer having at least one member directly connectible to the protruding portion of the anchor assembly.

9. The combination as defined in claim 8 wherein the sheath and retainer are constructed to maintain direct connection with the protruding end of the anchor while the retainer is disposed within the sheath.

10. An abdominal aortic repair device comprising:

an elongate tubular graft adapted to be positioned within a blood vessel, the graft having a proximal end, a distal end, and an axial length;

a self-expanding anchor assembly secured to the graft, the anchor assembly being adapted to inhibit migration of the graft when positioned at a desired location in a blood vessel, the anchor assembly having a proximal end, a distal end and an axial length greater than the axial length of the graft, at least the proximal end and the distal end of the anchor being resiliently expandable and connected to each other by at least two longitudinal segments that extend between the proximal and distal ends of the anchor, and each of the longitudinal segments being constructed and arranged to transmit a radial compression force through the longitudinal segments from one end of the anchor assembly to the other end of the anchor assembly, the proximal end of the anchor assembly being accessible and defining a connector for direct rigid connection to a delivery device.

* * * * *